(12) United States Patent
Smith

(10) Patent No.: US 7,094,529 B2
(45) Date of Patent: Aug. 22, 2006

(54) BUNYAVIRIDAL REAPER PROTEINS AND USES THEREFORE

(75) Inventor: Gary Keith Smith, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 784 days.

(21) Appl. No.: 10/203,081

(22) PCT Filed: Feb. 16, 2001

(86) PCT No.: PCT/US01/05275

§ 371 (c)(1),
(2), (4) Date: Aug. 5, 2002

(87) PCT Pub. No.: WO01/62936

PCT Pub. Date: Aug. 30, 2001

(65) Prior Publication Data

US 2003/0082527 A1 May 1, 2003

Related U.S. Application Data

(60) Provisional application No. 60/184,055, filed on Feb. 22, 2000.

(51) Int. Cl.
*C12Q 1/70* (2006.01)
*C12Q 1/02* (2006.01)
*C12N 5/00* (2006.01)
*C12N 5/10* (2006.01)

(52) U.S. Cl. .............. 435/5; 435/29; 435/375; 435/455; 435/183

(58) Field of Classification Search .............. 435/5, 435/29, 375, 183, 455; 514/1, 12
See application file for complete search history.

(56) References Cited

U.S. PATENT DOCUMENTS

2002/0081643 A1 * 6/2002 Wang et al. ............... 435/7.91

FOREIGN PATENT DOCUMENTS

WO     WO 98/01563     1/1998

OTHER PUBLICATIONS

Murphy. "Virus Taxonomy." In Fields Virology, Third Edition, Ed. B.N. Fields et al, Lippincott–Raven Publishers, Philadelphia, 1996. pp. 15–57.*
Printout of May, 2003 search for SEQ ID NO:2 on protein sequence databases A_Geneseq, PIR, SPTREMBL. (Edited to remove aligments falling well below 50% sequence similarity).*
Printout of first page of results for Nov., 2003 search of all virus proteins on NCBI database (National Center for Biotechnology Information, National Library of Medicine, National Institutes of Health).*
Thress et al (EMBO journal 17:6135–6143, 1998).*
Moffatt et al (Journal of Virology 72:3018–3028, Apr. 1998).*
Sol et al (Journal of Virology 73:8762–8770, Oct. 1999).*
Cipens et al., "Reaper gene RPR product has common elements of structure with gamma–invariant chain, p53, MMTV and M proteins," *Proceedings of the Latvian Acadamey of Sciences Section B Natural Exact* 50(4–5):214–219 (1996).
Goyal et al., "Induction of apoptosis by *Drosophila* reaper, hid and grim through inhibition of IAP function," *EMBO* 19(4):589–597 (Feb. 2000).
Kang et al., "Apoptosis is induced by hantaviruses in cultured cells," *Virology* 264(1):99–105 (Nov. 1999).
Pekosz et al., "Induction of apoptosis by La Crosse virus infection and role of neuronal differentiation and human bcl–2 expression in its prevention," *Journal of Virology* 70(8):5329–5335 (1996).
Planchon et al., "BCL–2 protects against beta–lapachone–mediated caspase 3 activationand apoptosis in human myeloid leukemia (HL–60) cells," *Oncology Reports, National Hellenic Research Foundation, Athens, GR* 6(3):485–492 (1999).
Adams et al., "The Bcl–2 protein family: arbiters of cell survival," *Science* 281:1322–1326 (Aug. 1998).
Avdonin et al., "Apoptotic proteins Reaper and Grim induce stable inactivation in voltage–gated $K^+$ channels," *Proc. Natl. Acad. Sci. USA* 95:11703–11708 (Sep. 1998).
McCarthy et al., "Apoptosis induced by *Drosophila* Reaper and Grim in a human system," *The Journal of Biological Chemistry* 273(37):24009–24015 (Sep. 1998).
Thress et al., "Scythe: a novel reaper–binding apoptotic regulator," *The EMBO Journal* 17(21):6135–6143 (1998).
Thress et al., "Reaper–induced dissociation of a Scythe–sequestered cytochrome c–releasing activity," *The EMBO Journal* 18(20):5486–5493 (1999).

* cited by examiner

*Primary Examiner*—Mary E. Mosher
(74) *Attorney, Agent, or Firm*—Virginia G. Campen

(57) ABSTRACT

Viral proteins with sequence and functional similarity to the drosophila cell death protein known as Reaper are provided. Reaper plays an important role in the apoptotic pathway. Methods using the viral proteins and nucleotides encoding such proteins are described.

21 Claims, 4 Drawing Sheets

Alignment of Reaper, using Clustal method with PAM 250 residue weight.
Underlining: residues that match L3163Reaper1.pro within 3 distance units;

```
Majority:                        NMSHPQVQMD LILMQGMWHL VLNMGNLSIC QPLGSSSLMP U47139SanAngeloVirus.pro         MMSHQPVQMD LILMQGIWHS VLNMGSRSVC LQLGSSSSMP
P03514SnowshoeHareVirus.pro      MMSHQQVQMD LILMQGIWHS VLNMQNQSIL LQLGSSSSMP
K00108LaCrosseProtein.pro        MMSHQQVQMD LILMQGIWTS VLKMQNHSTL LQLGSSSSML
U12797CalEncephVirProtein.pro    MMSHPQVQMD LILMQGMWTS VLNMGNQLTL LQLGSSSSMP
U12798JerrySloughVirus2ndORF.    MMSHPQVQMD LIQMQGLWHL WLTTESLSIC QPLGSSSLMQ
u12796JamestownCanyon2ndORF.     MMSHPQVQMD LIQMQGLWHL WLTTESLSIC QPLGSSSLMQ
u12801KeystoneVirus2ndORF.       MMSHPQVQMD LILMQGMWHL WLTMGSRSVC QPLGSSSLMP
u12802MelaoVirus2ndORF.          MMSHQQVQMD LIQMQGIWHL QLRMGKLSIC QPLGSSSLMP
U12803TrivittatusVirus2ndORF.    MMLHQQVQTD LIPMQGMWHL LLHMPDRTIF LLLGSSSSML
U31989MorroBayVirus2ndORF.       MMSHPQVQMD LILMQGMWTS VLNMGNRLTL LQLGSSSSMP
U47138InkooVirus2ndORF.          MMSHPQVQMD LIQMQGLWHL WLTMENLLIW QPLGSSSLMQ
U47140SeradoNavioVirus2ndORF.    MMSHQPVQMD LIQMQGLWHL WLVMGSRSIL QPLESSSLMP
U47141SouthRiverVirus2ndORF.     MMSHPQVQMD LIQMQGLWHL WLTMENLSIC QPLGSSSLMQ
X73468LumboVirus2ndORF.          MMSHPPVQMD LILMQGMWTF VLNMENQSIS IPLGSFSLMP
Z68497TahynaVirus2ndORF.         MMSHPPVQMD LILMQGMWTF VLNMENQSIS IPLGSFSLMP
L31631Reaper1.pro                M---------  ---------- ---------- ---AVAFYIP
U61976GrimPiece.pro              M---------  ---------- ---------- ---AIAFYIP Majority:                        QKPKLLSLVS RRGKLILNLE SGRWRLSIII FLETGTTQLV U47139SanAngeloVirus.pro         QKPKLLSRVN QRGKQILNLA SGRWRLSIII FLETGTIQLT
P03514SnowshoeHareVirus.pro      QRPRLLSRVS QRGRQILNLE SGRWRLSIII FLETGTIQLT
K00108LaCrosseProtein.pro        QRPRLLSRVS QRGRLTLNLE SGRWRLSIII FLETGTTQLV
U12797CalEncephVirProtein.pro    QRPRLLSRVS QRGKLILNLA SGRWRLSIII GQQTGTIQLV
U12798JerrySloughVirus2ndORF.    QKPKLLSLVN RSGKLLLSLE SGRQWRSSIII FLETGTTQLV
u12796JamestownCanyon2ndORF.     QKPKLLSLVN RSGKLLLSLE SGRQWRSSIII FLETGTTQLV
u12801KeystoneVirus2ndORF.       QKPKLLSLVS RSGRLHLSLE SGRWRSSIII FLETGTTQLV
u12802MelaoVirus2ndORF.          QKPKLLSLVN RRGKLLLNLE TGRWKLSTII FLETGTTQLV
U12803TrivittatusVirus2ndORF.    PRPRMLSREN QRGRLVLNLA SGRWRWSIII FLATGTIQLV
U31989MorroBayVirus2ndORF.       QKPRLLSRVS QRGKLILNLA SGRWRLSIII FQQTGTIQLV
U47138InkooVirus2ndORF.          QKPKLLSLVN RSGKLLLNLE SGRWRLSIII FLETGTTQLV
U47140SeradoNavioVirus2ndORF.    QKPKLLSLAS RRGKLLLSLE TGRWRLSIII FLETGTTQLV
U47141SouthRiverVirus2ndORF.     QKPKLLSLVN RSGRLILNLE SGRWRLSIII FLETGTTQLV
X73468LumboVirus2ndORF.          LRPRLLSLVS RRGRLVLNLE SGRWRSSIII FLETGTTQLI
Z68497TahynaVirus2ndORF.         QKPKLLSLVS RRGRLVLNLE SGRWRSSIII FLETGTTQLI
L31631Reaper1.pro                DQATLLREAE QKEQQILRLR ESQWRFLATV VLE--TLRQY
U61976GrimPiece.pro              DQAQLLARS- ---------  ---------- ----------
```

FIG. 1A.

| | | | |
|---|---|---|---|
| Majority: | TTILPSTGFQ | -DI----- | (SEQ ID NO: 2) |
| U47139SanAngeloVirus.pro | TSILPSTDCL | -DTWLDGF | (SEQ ID NO: 3) |
| P03514SnowshoeHareVirus.pro | ATILPSTDCQ | -DI | (SEQ ID NO: 4) |
| K00108LaCrosseProtein.pro | TTILPSTDYL | -GI | (SEQ ID NO: 5) |
| U12797CalEncephVirProtein.pro | TTILPSTASQ | -DTLPDGS | (SEQ ID NO: 6) |
| U12798JerrySloughVirus2ndORF. | TTILPSIGFQ | -DI | (SEQ ID NO: 7) |
| u12796JamestownCanyon2ndORF. | TTILPSIGFQ | -DI | (SEQ ID NO: 8) |
| u12801KeystoneVirus2ndORF. | TTILPCTGFQ | -DI | (SEQ ID NO: 9) |
| u12802MelaoVirus2ndORF. | TTILPSIGFQ | -DILPDGC | (SEQ ID NO: 10) |
| U12803TrivittatusVirus2ndORF. | TTILPSTEFQ | -AISQDGF | (SEQ ID NO: 11) |
| U31989MorroBayVirus2ndORF. | TTILPSTASQ | -DTLPDGS | (SEQ ID NO: 12) |
| U47138InkooVirus2ndORF. | TTILPSTGFL | -DT | (SEQ ID NO: 13) |
| U47140SeradoNavioVirus2ndORF. | TTILPSTEFQ | -DI | (SEQ ID NO: 14) |
| U47141SouthRiverVirus2ndORF. | TTILPSTGFL | -DI | (SEQ ID NO: 15) |
| X73468LumboVirus2ndORF. | TTILPSTGCQ | -GIWLDGC | (SEQ ID NO: 16) |
| Z68497TahynaVirus2ndORF. | TTILPSTGCT | -GIWLDGC | (SEQ ID NO: 17) |
| L31631Reaper1.pro | TSCHPKTGRK | SGKYRKPSQ | (SEQ ID NO: 1) |
| U61976GrimPiece.pro | ---------- | ---YQQNGQ | (SEQ ID NO: 18) |

BUNYAVIRIDAL REAPER PROTEINS AND USES THEREFORE

This application is filed pursuant to 35 U.S.C. §371 as a United States National Phase Application of International Application No. PCT/US01/05275 filed Feb. 16, 2001, which claims priority from U.S. Provisional Application No. 60/184,055 filed Feb. 22, 2000.

FIELD OF THE INVENTION

The present invention relates to a viral cell death gene and the protein expressed thereby, and in particular, but not exclusively, to nucleotide sequences, expression vectors, cell lines, antibodies, screening methods, compounds, methods of production and methods of treatment, related to them.

BACKGROUND OF THE INVENTION

Apoptosis is a form of programmed cell death, by which an organism eliminates extraneous or harmful cells. Apoptosis plays a role in normal development and homeostasis, as well as in diseases such as cancer and neurodegenerative diseases.

Apoptosis occurs via the activation of intrinsic cell-suicide programs; activation is regulated by many different signals, both intracellular and extracellular. Various viral and metazoan apoptosis inducer genes have been identified; inhibitors of apoptosis (IAP) proteins have also been identified that act to suppress apoptosis.

At least three apoptotic activator proteins have been identified in *Drosophila melanogaster:* reaper (rpr), head involution defective (hid) and grim. The N-terminal sequences of these proteins are highly conserved. Avdonin et al., *Proc. Natl. Acad. Sci. USA* 95:11703 (1998). Proteins that inhibit apoptosis (IAPs) have also been identified in *Drosophila*. Hay et al., *Cell* 83:1253 (1995); Wing et al., *Cell Death Differ.* 5:930 (1998).

The product of the reaper gene is required for programmed cell death in *Drosophila*. Cell death induced by the reaper protein has been shown to be blocked by the baculovirus p35 protein, a viral product that inactivates proteases. White et al., *Science* 271:805 (1996).

The *Drosophila* Grim protein is also an activator of apoptosis, independent of Reaper. Expression of Grim RNA coincides with the onset of programmed cell death during embryonic development, and ectopic induction of grim has been show to trigger extensive apoptosis in transgenic animals and in cell culture. Similar to the Reaper protein, cell killing by grim can be blocked by coexpression of the viral p35 product. The grim gene product has been postulated to function in a parallel cell death signalling regime that activates a common set of downstream apoptotic effectors. Chen et al., *Genes Dev.* 10:1773–1782 (1996).

Viral infection of host cells, and replication therein, is often associated with inhibition of apoptosis to enable viral replication and the subsequent stimulation apoptosis of the host cells for viral particle release. Certain viral gene products have been shown to specifically inhibit or induce apoptosis. However, many viruses additionally encode proteins that inhibit apoptosis, prolonging the survival of infected cells and thereby aiding viral replication or viral persistence in the host.

SUMMARY OF THE INVENTION

A first aspect of the present invention is a method of screening compounds for the ability to modulate the apoptotic effects of viral reaper proteins on cells. The protein may consist of or comprise an amino acid sequence selected from SEQ ID NOs:2–17.

According to another aspect of the invention there is provided a method of using nucleotide sequences encoding viral reaper proteins or a variant thereof, or a nucleotide sequences which are complementary thereto. Preferably the nucleotide sequence is a cDNA sequence. Particularly preferably the nucleotide sequence is selected from SEQ ID NOs:2–17.

According to another aspect of the invention there is provided a method of treating cells using viral reaper proteins, to affect the cell's apoptotic mechanism.

According to another aspect of the invention, there is provided a method of using expression vectors comprising a nucleic acid sequence as referred to above that is capable of expressing a viral reaper protein.

According to another aspect of the invention there is provided a method of treatment or prophylaxis of a disorder that is responsive to modulation of apoptosis by a viral reaper protein modulator, the method comprising administering to a subject in need thereof an effective amount of a viral reaper protein modulating compound. Preferably the disorder is selected from viral infections in mammalian subjects.

According to a further aspect of the invention there is provided use of a compound that modulates viral reaper protein activity in a method of formulating a medicament for treatment or prophylaxis of a disorder that is responsive to modulation of viral reaper protein activity, in a subject in need of such treatment. Preferably the disorder is selected from viral infections in mammalian subjects.

BRIEF DESCRIPTION OF THE FIGURES

The present invention will be further described by way of example and with reference to the following figures:

FIGS. 1A and 1B show the amino acid sequences of the nonstructural (NSs) viral proteins from fifteen different virus, aligned with the amino acid sequence of the complete Reaper protein (SEQ ID NO: 1) and a portion of the Grim protein from *Drosophila melanogaster* (SEQ ID NO:18). A majority sequence for the viral reaper protein is provided as SEQ ID NO:2.

DETAILED DESCRIPTION OF THE INVENTION

Figure 2:
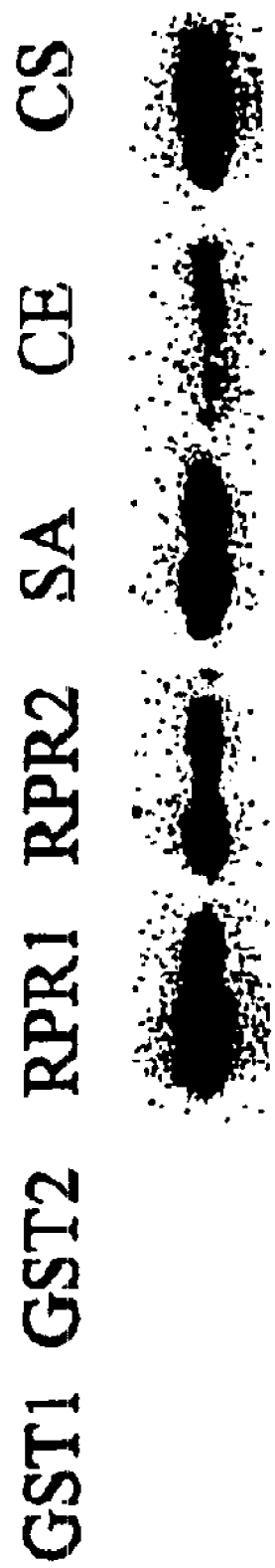
FIG. 2 shows Western blot results indicating binding of various reaper proteins to Xenopus scythe protein (Example 4). RPR1 and RPR2 indicate preparations of *Drosophila* Reaper, SA indicates San Angelo virus reaper, and CE indicates California Encephalitis virus reaper; GST1 and GST2 are preparations of glutathione-S-transferase used as controls.

Viral proteins with sequence similarity to the *Drosophila melanogaster* Reaper protein have been identified, and shown to be capable of activating caspases in vertebrate cell-based assay. Cellular death by apoptosis is, with only some exceptions, executed by the family of proteases known as caspases. The caspases are synthesized as inactive zymogens and activated during apopototic pathways. (Chinnaiyan and Dixit, *Curr. Biol.* 6:555 (1996); Muzio et al, *J. Biol. Chem.* 273:2926 (1998); Yang et al., *Mol. Cell.* 1:319 (1998); Zou et al., *Cell* 90:405 (1997)). Caspase activation (and thus ultimately apoptosis) can be blocked by the IAP (inhibitor of apoptosis) proteins and anti-apoptotic members of the Bcl-2 family (Adams and Cory *Science* 281:1322 (1998); Deveraux and Reed, *Genes Dev.* 13:239 (1999)).

The present viral genes and their expression products provide useful screening assays for the identification and development of novel pharmaceutical agents, including agonists and antagonists of the viral reaper proteins, and compounds able to enhance or inhibit caspase activation and/or cellular apoptosis; such compunds may be used in the treatment and/or prophylaxis of disorders such as cancer and viral infections. In particular, the present methods are useful in identifying compounds that enhance or inhibit apoptosis due to caspase activation.

Accordingly, it is an object of the present invention to provide methods of using isolated viral reaper proteins. Other objects of the present invention will become apparent from the following detailed description thereof.

The present inventors identified viral proteins with sequence similarity to the *D. melanogaster* Reaper protein. More particularly, the present inventors determined that the non-structural protein (NSs) of viruses of the genus *Bunyavirus* exhibited sequence similarity to the *Drosophila* Reaper protein.

Viruses of the genus *Bunyavirus* (family Bunyaviridae) are single stranded RNA negative-strand viruses that infect vertebrates. There are 18 antigenic groups of the genus *Bunyavirus* (at least 161 viruses) and several additional ungrouped viruses.

The California encephalitis virus, LaCrosse virus, San Angelo virus, Snowshoe Hare virus, Jerry Slough virus, Jamestown Canyon virus, Keystone Virus, Melao virus, Trivittatus virus, Morro Bay virus, Inkoo virus, Serra do Navio virus, South River virus, Lumbo virus, and Tahyna virus are each members of the genus *Bunyavirus*. The genome consists of a large (L) RNA, a medium (M) RNA, and a small (S) RNA. The nonstructural protein (NSs protein) of these viruses is encoded by the small (S) RNA, and is induced in virus-infected cells (Fuller and Bishop (1982) J. Virol. 41, 643–648). The NSs protein of each of these viruses was found by the present inventors to have sequence similarity to the *Drosophila* Reaper protein (FIG. 1).

A nucleotide sequence encoding *D. melanogaster* Reaper protein is given at GenBank Accession No. L31631; the protein sequence is provided at Acc. No. AAA18983. The amino acid sequence of the *Drosophila* cell death protein GRIM is provided at GenBank Acc. No. AAC47727.

The nucleotide sequence encoding San Angelo virus (Prototype VR723) nucleocapsid and non-structural proteins is provided at GenBank Accession U47139. The amino acid sequence of San Angelo virus NSs protein is provided at Acc No. AAC5335.

The amino acid sequence of a NSs of the Snowshoe Hare virus is provided at Accession No. P03514; the nucleotide sequence of a small (S) viral RNA species of snowshoe hare virus is provided at Acc. No. J02390. See also Bishop et al., *Nucleic Acids Res.* 10 (12), 3703–3713 (1982).

The nucleotide sequence of a La Crosse virus small RNA segment is provided at GenBank Accession No. K00108.

The amino acid sequence for a La Crosse Virus non structural protein can be found at Accession No. AAA42780.1

The nucleotide sequence for a California Encephalitis virus small RNA segment, including the nucleocapsid and NSs protein genes, is provided at GenBank Accession No U12797; the amino acid sequence of the viral NSs protein can be found at Acc. No. AAC54056.1. See also Bowen, M. D., et al. *J. Gen. Virol.* 76: 559–572 (1995).

The nucleotide sequence encoding Jerry Slough Virus NSs protein is provided at GenBank Accession No. U12798; the amino acid sequence of the viral NSs protein can be found at Acc. No. AAC54048.

The nucleotide sequence encoding Jamestown Canyon Virus NSs protein is provided at GenBank Accession No. U12796; the amino acid sequence of the viral NSs protein can be found at Acc. No. AAC54044.

The nucleotide sequence encoding Keystone Virus NSs protein is provided at GenBank Accession No. U12801; the amino acid sequence of the viral NSs protein can be found at Acc. No. 54054.

The nucleotide sequence encoding Melao Virus NSs protein is provided at GenBank Accession No. U12802; the amino acid sequence of the viral NSs protein can be found at Acc. No. AAB60560.

The nucleotide sequence encoding Trivittatus Virus NSs protein is provided at GenBank Accession No. U12803; the amino acid sequence of the viral NSs protein can be found at Acc. No. AAB60562.

The nucleotide sequence encoding Morro Bay Virus NSs protein is provided at GenBank Accession No. U31989; the amino acid sequence of the viral NSs protein can be found at Acc. No. AAC55125.

The nucleotide sequence encoding Inkoo Virus NSs protein is provided at GenBank Accession No. U47138; the amino acid sequence of the viral NSs protein can be found at Acc. No. AAC55333.

The nucleotide sequence encoding Serra do Navio Virus NSs protein is provided at GenBank Accession No. U47140; the amino acid sequence of the viral NSs protein can be found at Acc. No. AAC55337.

The nucleotide sequence encoding South River Virus NSs protein is provided at GenBank Accession No. U47141; the amino acid sequence of the viral NSs protein can be found at Acc. No. AAC55339.

The nucleotide sequence encoding Lumbo Virus NSs protein is provided at GenBank Accession No. X73468; the amino acid sequence of the viral NSs protein can be found at Acc. No. CAA51852.

The nucleotide sequence encoding Tahyna Virus NSs protein is provided at GenBank Accession No. Z68497; the amino acid sequence of the viral NSs protein can be found at Acc. No. Z68497.

The present viral Reaper proteins act as apoptotic modulating proteins, affecting apoptosis in host cells. Discovery of these viral proteins provides methods to screen compounds for the ability to block or enhance the viral reaper function, and the use of compounds identified thereby to modulate apoptosis. Apoptosis may also be modulated by the administration of viral reaper proteins (or a functional variant or fragment thereof) to a cell. Administration may utilize isolated nucleic acid molecules encoding the viral reaper proteins, vectors containing such molecules, and host cells transfected with the same. The host cells may be any cell suitable for cultivation of the virus, as is known in the art. More preferred are vertebrate cells, including mammalian cells.

The present proteins (and functional variants and fragments thereof) and nucleotides expressing the same, are useful in several settings. Where a virus is being cultivated, either in cell culture or in vivo, the presently identified viral reaper proteins (and/or the compounds discovered in the screening assays described above) may be used to modulate apoptosis of infected host cells, by administering the protein or compounds to the cells. Inhibiting apoptosis of the host cell is useful where further replication of the virus within the host cell can be attained and is desirable. Inducing apoptosis of the host cell is useful where infection of additional cells is desirable, in harvesting virus, or where it is necessary and desirable to terminate survival of the host cell in order to halt further viral replication/propagation.

Additionally, the present proteins and/or compounds discovered using the present screening assays, may be used in the treatment of certain conditions involving aberrant apoptosis of a subject's cells. Viral reaper proteins and/or such compounds may be administered to a preselected population of cells in a subject, to modulate apoptosis of those cells. Such a method is useful in conditions where the normal apoptotic mechanism of the subject's cells is altered, e.g., in cancer and neoplastic growths. Such a method is also useful in treating viral infections.

The present invention also provides a method to screen compounds for the ability to inhibit or enhance the function of the viral reaper proteins (e.g., to act as antagonists or agonists of the viral reaper protein function). Such compounds will be useful in the above-described methods. Such compounds may be administered alone, to act upon endogenous viral reaper proteins produced within an infected host cell; or they may be administered to a cell in conjunction with exogenous viral reaper protein where needed (e.g., where the compound enhances the effects of the exogenous viral reaper protein).

As used herein, "sequence similarity" of proteins refers to the similarity of the amino acid sequence between two proteins. Various computer programs are commercially available that determine sequence similarity, and are known to those skilled in the art. The degree of sequence similarity takes into consideration both amino acid residues that are identical, as well as those that are conservative amino acid substitutions (as is known in the art).

"Sequence similarity" as used in the present specification and claims refers to DNA sequences, (or RNA sequences; or amino acid sequences) that have only slight and non-consequential sequence variations between them. In this regard, 'slight and non-consequential sequence variations' mean that the sequences will be functionally equivalent. Functionally equivalent sequences will function in substantially the same manner to produce substantially the same results.

As used herein, two amino acid sequence that have substantial "sequence similarity" are those having at least about 50% or 55% sequence similarity, and preferably at least about 60%, 65%, 70%, 75%, 80%, 85%, or even about 90% or 95% similarity. Changes in the amino acid sequence of peptides can be guided by known similarities among amino acids and other molecules or substituents in physical features such as charge density, hydrophobicity, hydrophilicity, size and configuration, etc. For example, the amino acid Thr may be replaced by Ser and vice versa, and Leu may be replaced by Ile and vice versa.

The peptides of the present invention include not only natural amino acid sequences, but also peptides which are analogs, chemical derivatives, or salts thereof. The term "analog" or "conservative variation" refers to any polypeptide having a substantially identical amino acid sequence to the peptides identified herein, and in which one or more amino acids have been substituted with chemically similar amino acids. For example, a polar amino acid such as glycine or serine may be substituted for another polar amino acid; a basic amino acid may be substituted for another basic amino acid, or an acidic amino acid may be substituted for another acidic amino acid; or a non-polar amino acid may be substituted for another non-polar amino acid. There term "analog" or "conservative variation" as used herein also refers to a peptide which has had one or more amino acids deleted or added to a polypeptide of the present invention, but which retains a substantial sequence similarity (at least about 85% sequence similarity, and preferably at least 90%, 95%, 98% or even 99% sequence similarity), where the peptide retains the viral reaper protein function or generates an antagonistic viral reaper function.

Given the amino acid sequence of a particular viral protein, a nucleotide sequence encoding the protein can be readily determined, and a nucleotide molecule encoding the protein can be prepared.

The present invention also encompasses the use of nucleotide molecules that encode viral reaper proteins. Examples of such nucleotide sequences are below. Due to the degeneracy of the genetic code, one skilled in the art will be able to readily devise alternative nucleotide sequences that encode a given protein, where the amino acid sequence of the protein is known.

```
nucleotide sequence encoding Drosophila melanogaster Reaper Protein
L31631
                                                        (SEQ ID NO:19)
atggcagtgg cattctacat acccgatcag gcgactctgt tgcgggaggc ggagcagaag   60
gagcagcaga ttctccgctt gcgggagtca cagtggagat tcctggccac cgtcgtcctg  120
gaaaccctgc gccagtacac ttcatgtcat ccgaagaccg gaagaaagtc cggcaaatat  180
cgcaagccat cgcaatga nucleotide sequence encoding San Angelo Virus NSs protein
U47139
                                                        (SEQ ID NO:20)
atgatgtcgc atcaaccggt gcaaatggat ttgatcctga tgcagggtat ctggcattct   60
gtgttaaaca tggggagtcg atcagtttgt cttcagttag gatcttcttc ctcaatgccg  120
```

-continued

```
caaaagccaa agctgctctc tcgcgtaaac cagagaggaa agcaaatcct aaatttggcg    180
agtggcaggt ggagattgtc aataatcatt ttcctggaaa caggaacaat ccaattgaca    240
acctcgatct taccatccac agattgtctg gatacctggc tagatgggtt ctag          294
``` nucleotide sequence encoding Snowshoe Hare Virus
UP03514
(SEQ ID NO:21)
```
atgatgtcgc atcaacaggt gcaaatggat ttgatcctga tgcagggtat atggcattct     60
gtgttaaata tgcagaatca gtcaatcttg ctgcagttag atcttcttc ctcaatgccg     120 caaaggccaa ggctgctctc tcgcgtaagc cagagaggaa ggcaaatcct aaatttggag    180
agtggcaggt ggaggttgtc aataatcatt ttcctggaaa caggaacaat ccaattaaca    240
gcgacgatct taccatccac agattgtcag gatatttag                            
``` nucleotide sequence encoding LaCrosse Virus NSs protein
K00108
(SEQ ID NO:22)
```
atgatgtcgc atcaacaggt gcaaatggat ttgatcctga tgcagggtat atggacttct     60
gtgttaaaaa tgcagaatca ctcaaccttg ctgcagttag atcttcttc ctcaatgctg     120 caaaggccaa ggctgctctc tcgcgtaagc cagagaggaa ggctaaccct aaatttggag    180
agtggcaggt ggaggttatc aataatcatt ttcctggaaa caggaacaac ccaattggta    240
acaacgatct taccatccac agattatctg ggtatttag                            
``` nucleotide sequence encoding California encephalitis NSs protein
U12797
(SEQ ID NO:23)
```
atgatgtcgc atccacaggt gcaaatggat ttgatcctga tgcagggtat gtggacttct     60
gtgctaaaca tggggaatca attaaccttg ctgcagttag atcttcttc ctcaatgccg     120 caaaggccaa ggctgctctc tcgcgtaagc cagagaggaa agctaatcct aaatttggcg    180
agtggcaggt ggaggttgtc aataatcatt ttccagcaaa caggaacaat ccaattggta    240
acaacgatct taccatccac cgcatctcag gataccttgc cagatgggtc ctag          294
``` nucleotide sequence encoding Jerry slough virus NSs protein
U12798
(SEQ ID NO:24)
```
atgatgtcgc atccacaggt gcaaatggat ttgatccaga tgcagggttt gtggcattta     60
tggctgacca cggagagtct atcaatctgt cagccgttag atcttcttc cttaatgcag     120 caaaagccaa agctgctctc gctcgtaaac cggagcggaa agctactcct aagtttggag    180
agtggcaggt ggagatcatc aataatcatt ttcctggaaa caggaacaac ccaattggta    240
acaacgatct taccatccat aggctttcag gatatctag                           279
```

Nucleotide sequence encoding Jamestown Canyon virus NSs protein
U12796
(SEQ ID NO:25)
```
atgatgtcgc atccacaggt gcaaatggat ttgatccaga tgcagggttt gtggcattta     60
tggctgacca cggagagtct atcaatctgt cagccgttag atcttcttc cttaatgcag     120 caaaagccaa agctgctctc gctcgtaaac cggagcggaa agctactcct aagtttggag    180
agtggcaggt ggagatcgtc aataatcatt tttctggaaa caggaacaac ccaattggta    240
acaacgatct taccatccat aggctttcag gatatctag                           279
```

Nucleotide sequence encoding Keystone Virus NSs protein
U12801
(SEQ ID NO:26)
```
atgatgtcgc atccacaggt gcaaatggat ttgatcctga tgcagggtat gtggcattta     60
tggctaacca tggggagtcg atcagtctgt caaccgttag atcttcttc cttaatgccg     120 caaaagccaa agctgctctc actcgtaagc cggagcggaa ggctacacct aagtttggag    180
```

-continued

```
agtggcaggt ggagatcgtc aataatcatt ttcctggaaa caggaacaac ccaattggta    240
acaacgatct taccttgcac cggatttcag gatatctag                            279
```

Nucleotide sequence encoding Melao Virus NSs protein
U12802
(SEQ ID NO:27)
```
atgatgtcgc atcaacaggt gcaaatggat ttgatccaga tgcagggtat ctggcattta    60
caattgcgca tggggaagct atcaatttgt cagccgttag gatcttcttc cttaatgccg    120
caaaagccaa agctgctctc tctcgtaaac cggagaggaa agctactcct aaatttggag    180
actggcaggt ggaaattgtc aacaatcatt ttcctggaaa caggaacaac ccaattggta    240
acaacgatct taccatccat cggctttcag gatatcttgc cagatgggtg ctag          294
```

Nucleotide sequence encoding Trivittatus Virus NSs protein
U12803
(SEQ ID NO:28)
```
atgatgctcc atcaacaggt gcaaacggat ttgatcccga tgcagggtat gtggcattta    60
ttgctgcaca tgccggatcg tacgatcttt ctgctgttag gatcttcttc ctcaatgctg    120
ccaaggccaa gaatgctctc tcgagaaaac cagagggaa ggttagtatt aaatttggcg     180
agtggtcggt ggaggtggtc aataatcatt ttcctggcaa caggaacaat ccaattggta    240
acaacgatct taccatccac agaatttcag gctatctcgc aagatggggtt ctag         294
```

Nucleotide sequence encoding Morro Bay Virus NSs protein
U31989
(SEQ ID NO:29)
```
atgatgtcgc atccacaggt gcaaatggat ttgatcctga tgcagggtat gtggacttct    60
gtgctaaaca tggggaatcg attaaccttg ctgcagttag gatcttcttc ctcaatgccg    120
caaaagccaa ggctgctctc tcgcgtaagc cagagaggaa agctaatcct aaatttggcg    180
agtggcaggt ggagattgtc aataatcatt ttccagcaaa caggaacaat ccaattggta    240
acaacgatct taccatccac cgcatctcag gataccttgc cagatgggtc ctag          294
```

Nucleotide sequence encoding Inkoo Virus NSs protein
U47138
(SEQ ID NO:30)
```
atgatgtcgc atccacaggt gcaaatggat ttgatccaga tgcagggttt gtggcattta    60
tggctgacca tggagaatct attaatttgg cagccgttag gatcttcttc cttaatgcag    120
caaaagccaa agctgctctc gctcgtaaac cggagcggaa agctactcct aaatttggag    180
agtggcaggt ggagattgtc aataatcatt ttcctggaaa caggaacaac ccaattggta    240
acaacgatct taccatccac cggctttctg gatacttag                           279
```

Nucleotide sequence encoding Serra do Navio Virus NSs protein
U47140
(SEQ ID NO:31)
```
atgatgtcgc atcaaccggt gcaaatggat ttgatccaga tgcagggttt gtggcattta    60
tggctggtca tggggagtcg atcaatctta cagccgttag aatcttcttc cttaatgccg    120
caaaagccaa agctgctctc tctcgcaagc cggagaggaa agctactcct aagtttggag    180
actggcaggt ggagattgtc aataatcatt ttcctggaaa caggaacaac ccaattggta    240
acaacgatct taccatccac agaatttcag gatatttag                           279
```

Nucleotide sequence encoding South River Virus NSs protein
U47141
(SEQ ID NO:32)
```
atgatgtcgc atccacaggt gcaaatggat ttgatccaga tgcagggttt gtggcattta    60
tggctgacca tggagaatct atcaatctgt cagccgttag gatcttcttc cttaatgcag    120
caaaagccaa agctgctctc gctcgtaaac cggagcggaa ggctaatcct aaatttggag    180
agtggcaggt ggagattgtc aataatcatt ttcctggaaa caggaacaac ccaattggta    240
```

-continued
```
acaacgatct taccatccac cggctttctg gatatttag                    279
```

Nucleotide sequence encoding Lumbo Virus NSs protein
X73468
(SEQ ID NO:33)
```
atgatgtcgc atccaccggt gcaaatggat ttgatcctga tgcagggtat gtggactttt  60
gtgttaaaca tggagaatca atcaatctcc attccgttag gatcttttc cttaatgccg  120 ctaaggccaa ggctgctctc gctcgtaagc cggagaggaa ggctagtcct aaatttggag  180
agtggcaggt ggagatcgtc aataatcatt ttcctggaaa caggaacaac ccaattgata  240
acaacgatct taccatccac cggctgtcag ggtatctggc tagatgggtg ttag        294
```

Nucleotide sequence encoding Tahyna Virus NSs protein
Z68497
(SEQ ID NO:34)
```
atgatgtcgc atccaccggt gcaaatggat ttgatcctga tgcagggtat gtggacttct  60
gtattaaaca tggggaagca attaatctcc attccgttag gatcttcttc cttaatgccg  120
caaaagccaa agctgctctc gctcgtaagc cggagaggaa ggctagtcct aaatttggag  180
agtggcaggt ggaggtcgtc aattatcatt ttcctggaaa caggaacaac ccaattgata  240
acaacgatct taccatccac cggctgtacg ggtatttggc tagatgggtg ctag        294
```

Nucleotide sequences that have substantial sequence similarity to the nucleotide sequences disclosed herein, and that encode functional viral reaper proteins, are suitable for use in the methods of the present invention.

Thus, use of nucleotides that hybridize to nucleotide molecules encoding the viral reaper proteins of SEQ ID NOs:2–17 are also an aspect of this invention. Conditions which will permit other nucleotide molecules encoding viral reaper proteins to hybridize to the nucleotide sequences disclosed herein can be determined in accordance with known techniques. For example, hybridization of such sequences may be carried out under conditions of reduced stringency, medium stringency, or even high stringency conditions (e.g., conditions represented by a wash stringency of 35–40% formamide with 5× Denhardt's solution, 0.5% SDS and 1×SSPE at 37° C.; conditions represented by a wash stringency of 40–45% formamide with 5× Denhardt's solution, 0.5% SDS, and 1×SSPE at 42° C.; and conditions represented by a wash stringency of 50% formamide with 5× Denhardt's solution, 0.5% SDS and 1×SSPE at 42° C., respectively, to a nucleotide molecule encoding a viral reaper protein as disclosed herein in a standard hybridization assay. See J. Sambrook et al., Molecular Cloning: A Laboratory Manual (2d ed. 1989)). In general, sequences encoding functional viral reaper proteins that hybridize to the nucleotide sequences disclosed herein will have at least 30% sequence similarity, 50% sequence similarity, 75% sequence similarity, and even 95% sequence similarity or more with the nucleotide sequences encoding viral reaper proteins disclosed herein.

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

As referred to above, the present invention relates to methods of using isolated viral reaper proteins or isolated nucleotide molecules encoding viral reaper proteins. In the context of this invention the term "isolated" is intended to convey that the protein is not in its native state, insofar as it has been purified at least to some extent or has been synthetically produced, for example by recombinant methods. The term "isolated" therefore includes the possibility of the protein being in combination with other biological or non-biological material, such as cells, suspensions of cells or cell fragments, proteins, peptides, expression vectors, organic or inorganic solvents, or other materials where appropriate, but excludes the situation where the protein or nucleic acid molecule is in a state as found in nature.

As used herein, the term "viral reaper protein" comprises proteins having an amino acid sequence identical to that of a protein naturally expressed by a virus, and having the ability to induce caspase activation in a vertebrate cell. One method of assaying a protein for the ability to induce caspase activation in a vertebrate cell (*Xenopus oocytes*) is provided in the Examples section herein.

Routine methods, as further explained in the subsequent experimental section, can be employed to purify and/or synthesize the proteins according to the invention. Such methods are well understood by persons skilled in the art, and include techniques such as those disclosed in Sambrook J., Fritsch E. F. and Maniatis T., Molecular Cloning: a Laboratory Manual; 2$^{nd}$ Edition; CSH Laboratory Press (1989), the disclosure of which is included herein in its entirety by way of reference.

The term "variant" as used herein refers to peptides or proteins which retain the same essential characteristics (functional and structural) of the viral Reaper proteins for which sequence information is provided herein; such variants are intended to be included within the scope of the invention. For example, other peptides or proteins with greater than about 50%, 55%, 60% or 65%, preferably at least 75% and particularly preferably at least 80%, 90% or 95% sequence similarity with the sequences provided, are considered as variants of the proteins. Such variants may include the deletion, modification or addition of single amino acids or groups of amino acids within the protein sequence, as long as the peptide maintains the basic biological functionality of a viral Reaper protein. This biological functionality can be assessed by one skilled in the art using methods that are known in the art.

The term "protein" as used herein is also intended to include within its meaning shorter peptide or polypeptide sequences as well as complete proteins. For example therefore a peptide of only perhaps 15 amino acids in length is considered to fall within the scope of the invention as long as it demonstrates the basic biological functionality of a viral Reaper protein as described herein. In particular, but not exclusively, this aspect of the invention encompasses the situation when the protein is a fragment of the complete protein sequence and may represent a ligand binding region.

The invention also includes methods of using isolated nucleotide sequences that encode viral Reaper proteins or variants thereof, as well as isolated nucleotide sequences which are complementary thereto. The nucleotide sequence may be RNA or DNA including genomic DNA, synthetic DNA or cDNA. Preferably the nucleotide sequence is a DNA sequence and most preferably, a cDNA sequence. Nucleotide sequence information is provided herein for certain viral reapers. Such nucleotides can be isolated from virally infected cells or synthesised according to methods well known in the art, as described by way of example in Sambrook J, Fritsch E. F. and Maniatis T; Molecular Cloning: a Laboratory Manual; $2^{nd}$ Edition; CSH Laboratory Press (1989), the disclosure of which is included herein in its entirety by reference. The nucleotide molecules according to the invention have utility in production of the proteins according to the invention, which may take place in vitro, in vivo or ex vivo. The nucleotides may be involved in recombinant protein synthesis or indeed as therapeutic agents in their own right, utilised in gene therapy techniques. Nucleotides complementary to those encoding viral Reaper proteins of the present invention, or antisense sequences, may also be used in therapy, such as in strategies for down regulation of expression of the proteins of the invention.

The present invention also includes methods of using expression vectors that comprise nucleotide sequences encoding viral Reaper proteins or variants thereof. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Suitable vectors would be apparent to persons skilled in the art. By way of further example in this regard we refer to Sambrook J, Fritsch E. F. and Maniatis T; Molecular Cloning: a Laboratory Manual; $2^{nd}$ Edition; CSH Laboratory Press (1989), the disclosure of which is included herein in its entirety.

The invention also includes methods of using cell lines that have been modified to express viral reaper proteins. Such cell lines include transient, or preferably stable higher eukaryotic cell lines, such as vertebrate cells, mammalian cells or insect cells; lower eukaryotic cells, such as yeast; or prokaryotic cells such as bacterial cells. Preferred are bacterial, insect and vertebrate cells. As used herein, cells that have been "modified" to express viral reaper proteins are those that contain isolated nucleic acid molecules coding for a viral reaper protein, and excludes cells infected with a virus expressing viral reaper protein from a non-isolated nucleic acid (e.g., a naturally occurring virus).

According to another aspect, the present invention also relates to antibodies (either polyclonal or preferably monoclonal antibodies) which have been raised by standard techniques and are specific for the proteins or variants thereof according to the invention. Such antibodies could for example, be useful in purification, isolation or screening involving immuno precipitation techniques and may be used as tools to further elucidate the protein function, or indeed as therapeutic agents in their own right. Antibodies may also be raised against specific epitopes of the proteins according to the invention.

A further aspect of the present invention is the use of the proteins according to the invention in screening methods designed to identify those compounds that act as ligands for viral Reaper proteins, and/or that modulate viral Reaper protein activity. In general terms, such screening methods will involve contacting the protein concerned, or cell modified to express the protein concerned, with a test compound and then detecting any enhancement or inhibition of protein activity that results (compared to the activity that would occur in the absence of the test compound). The present invention also includes within its scope those compounds that are identified as possessing useful viral Reaper protein modulation activity, by the screening methods referred to above, and use of such compounds. The screening methods comprehended by the invention are generally well known to persons skilled in the art.

Another aspect of the present invention is the use of compounds that have been identified by screening techniques referred to above, or the use of an isolated viral reaper protein, in the treatment or prophylaxis of disorders which are responsive to modulation of viral Reaper protein activity, in a subject in need of such treatment. Preferably such subjects are vertebrates, and more preferably, mammals. The term "modulation", as used herein, refers to both agonism (enhancement) and antagonism (inhibition) of an activity. Thus modulation may consist of an increase (or a decrease or time delay) in caspase activation or cellular apoptosis, in response to administration of a viral reaper protein (or a compound identified by the screening methods described herein). The change in activity (increase or decrease) is compared to that which would occur in the absence of the added viral reaper protein (or compound). Such increase (or decrease) may be measured by any suitable method as is known to those skilled in the art, e.g., detecting caspase activation over time or counting the number of apoptotic cells in a population over a fixed time period. The modulation activity may be due to direct binding of a compound to the viral reaper protein, or due to the effects of the compound on a downstream element of the apoptotic process that is modulated by the viral Reaper protein. Disorders that are responsive to modulation of cellular apoptosis are those in which the signs, symptoms and/or pathological changes associated with the disorder can be diminished or improved by altering (increasing, decreasing or delaying) cellular apoptosis.

Methods of screening compounds comprise contacting a viral reaper protein with a test compound, or administering a test compound to a cell that contains or expresses a viral reaper protein. By contacting it is meant that the test compound and viral reaper protein are in such proximity that they are able to biologically interact. Administration of a compound to a cell refers to the placement of the compound within the cell interior, either by direct administration or by cellular uptake.

A particular method of screening a compound to determine whether the compound enhances or inhibits caspase activation utilizes vertebrate cell extracts (cell-free preparations) which are known to exhibit detectable caspase activation when functional viral reaper is added to the cell extract. As used herein, an increase in (or enhancement of) caspase activation includes an increase in total caspase activity, a faster rate of caspase activity, and/or a decreased time until caspase activity is detected, as well as other measures that will be apparent to those skilled in the art. As used herein, a decrease in (or inhibition of) caspase activation includes a decrease in total caspase activity, a slowed rate of caspase activity, and/or an increase in the time until caspase activity is first detected; as well as other measures that will be apparent to those skilled in the art. Other indicators of activation of the apoptotic pathway are known in the art, e.g., mitochondrial cytochrome c release, fragmentation of nuclei added to a cell extract preparation. The change in caspase activation (or other indicators of apoptosis) is compared between preparations that contain the test compound and control preparations that do not; however, such comparisons need not be a side-by-side comparison, where a control has previously been tested and has provided data for comparison.

As used herein, a compound with "viral reaper modulating activity" is one that is capable of enhancing or inhibiting viral reaper induced apoptosis or caspase activation. As used herein, apoptosis induced by a viral reaper protein is that caused by activation of the apoptotic pathway by the viral reaper.

Some specific examples of disorders that may be treated or prevented by administration of compounds identified in the screening techniques according to the present invention are viral infections and disorders of apoptosis (such as cancer and neoplastic growths). Mention of such disorders is by way of example only, and is not intended to be limiting on the scope of the invention as described.

The compounds identified according to the screening methods outlined above may be formulated with standard pharmaceutically acceptable carriers and/or excipients as is routine in the pharmaceutical art, and as fully described in Remmington's Pharmaceutical Sciences, Mack Publishing Company, Easton, Pa., 17th Ed, 1985, the disclosure of which is included herein in its entirety by way of reference.

The compounds may be administered via enteral or parenteral routes such as via oral, buccal, anal, pulmonary, intravenous, intraarterial, intramuscular, intraperitoneal, topical or other appropriate administration routes. Appropriate administration routes, effective amounts, and dosing regimes may be determined by one skilled in the art using methods known in the art, e.g., dosage/response studies.

The present invention will now be further described by way of example.

EXAMPLES

Example 1

Identification of Viral Reaper Proteins

Using Advanced Blast, Psi Blast, Edit Seq and Meg Align programs, 15 nonstructural viral proteins (or the in silico translated viral DNA for these proteins) were unexpectedly found to have sequence similarity to the *Drosophila melanogaster* Reaper protein.

The 15 viral proteins (or in silico translated DNAs) investigated were the non-structural proteins (NSs) of San Angelo virus (NSs) (SEQ ID NO:3); Snow Shoe Hare virus (SEQ ID NO:4); La Crosse virus (SEQ ID NO:5), California encephalitis virus (SEQ ID NO:6), Jerry Slough virus (SEQ ID NO:7), Jamestown Canyon virus (SEQ ID NO:8), Keystone virus (SEQ ID NO:9), Melao virus (SEQ ID NO:10), Trivittatus virus (SEQ ID NO:11), Morro Bay virus (SEQ ID NO:12), Inkoo virus (SEQ ID NO:13), Serra do Navio virus (SEQ ID NO:14), South River virus (SEQ ID NO:15), Lumbo virus (SEQ ID NO:16), and Tahyna virus (SEQ ID NO:17). The amino acid sequences of these proteins were compared to that of the *D. melanogaster* Reaper protein (SEQ ID NO:1) and a portion of the *D. melanogaster* Grim protein (SEQ ID NO:18) Results are shown in FIG. 1.

It was found that 59 amino acids of the 65 amino acid *drosophila* reaper protein aligned with 61 amino acids of the ~92 amino acid viral reaper protein (or in silico translated DNA) with 58% similarity and 29% identity. These points of alignment therefore provide for a consensus reaper sequence cross-species.

A majority sequence was prepared (SEQ ID NO:2).

Example 2

Function of Viral Reaper Proteins

Viral reaper activity is detected utilizing extracts prepared from *Xenopus* eggs as described in Thress, et al, 1998, *The EMBO Journal* 17:6135–6143. Briefly, an egg extract prepared as described, is treated with 10 to 1000 nanograms of viral reaper protein or a glutathione-S transferase (GST) fusion protein with viral reaper. Control extracts (without viral reaper) are also prepared. After incubation of the mixture, caspase enzyme activity is measured with the substrate DEVD-pNA by following the increase in absorbance at 405 nanometers. Proteins such as reaper that are apoptotic activators cause an acceleration of the production of caspase activity (compared to that seen in controls).

The presence of apoptotic inhibitors slows or reduces caspase activation in extracts where reaper is incubated with the extract (compared to extracts incubated with reaper that do not contain the apoptotic inhibitor).

Ectopic expression of *Drosophila* Reaper has also been shown to induce caspase activation and apoptosis in mammalian cells such as human MCF7 breast carcinoma cells (McCarthy & Dixit, *J. Biol. Chem.* 273:24009 (1998)).

Example 3

Screening for Compounds That Exhibit Viral Reaper Modulating Activity

A cell culture of cells susceptible to viral Reaper-induced effects is established. The viral Reaper protein is administered to the cells (e.g., via transfection with a suitable plasmid and optionally a reporter protein such as B-galactosidase; or by direct administration of the viral reaper protein to the cell). A test compound is also administered to a test population of the cells. Administration of the test compound may occur prior to, concurrently with, or after administration of the viral Reaper protein. The effect of administration of the test compound on apoptosis of cells is compared to a control population of cells that did not receive the test compound. Significant differences in apoptosis (and/or caspase activation or other indicators of apoptosis) between the test and control cells indicates that the test compound modulates viral reaper protein activity.

Alternatively, extracts prepared from *Xenopus* eggs are used as described herein to test compounds for viral reaper-modulating effects. The test compound is included in an assay as described herein, and caspase activity in cells receiving the test compound is compared to control cells that do not receive the test compound. Significant differences in caspase activity production between the test and control extracts indicates that the test compound modulates viral reaper protein activity.

Example 4

Binding of *Drosophila* and Viral Reaper to Scythe

Glutathione S-transferase, *Drosophila* reaper, and two viral reaper proteins were examined to detect the ability to bind to scythe protein. It has previously been shown that *drosophila* reaper binds to *Xenopus* scythe protein to induce apoptosis in *Xenopus* oocytes. Scythe has been indicated as an apoptotic regulator that is an essential component in reaper-induced apoptosis; immunodepletion of scythe from *Xenopus* egg extracts prevents reaper-induced apoptosis without affecting apoptosis triggered by activated caspase. (Thress et al., *EMBO J* 17:6135–43 (1998); Evans et al, *EMBO J* 16:7372–81 (1997); Thress et al., *EMBO J* 18:5486 (1999)).

Glutathione S-transferase (GST), a *Drosophila* Reaper-GST construct (RPR), San Angelo virus reaper—GST construct (SA), and California Encephalitis virus reaper—GST construct (CE) were produced in BL21 bacterial strains (using standard techniques as are known in the art) and purified using glutathione sepharose beads. Two preparations of GST prepared by two different individuals were utilized as controls (GST1 and GST2); two preparations of *Drosophila* reaper prepared by two individuals were also used (RPR1 and RPR2). The *Xenopus* crude egg extract was prepared as described in Evans et al., *EMBO J*, 16:7372 (1997) and Thress et al., *EMBO J*, 17:6135 (1998).

The beads were incubated in *Xenopus* crude egg extract for an hour. The beads were then washed several times in egg lysis buffer (ELB; 250 mM sucrose, 2.5 mM MgCl2, 1.0 mM dithiothreitol (DTT), 50 mM KCl, 10 mM HEPES), pH 7.4, boiled, and run in an SDS-PAGE gel (using techniques as are well-known in the art) and subjected to Western analysis (using techniques that are well known in the art) to detect binding of scythe to the beads. An aliquot of *Xenopus* crude egg extract (CS) without any reaper or GST was also run on SDS-PAGE gel as a positive control.

As shown in FIG. 2, no binding was seen with either of the two GST preparations. *Drosophila* reapers (RPR1 and RPR2) bound scythe; the *Xenopus* crude egg extract (CS), which contains scythe, was included to show the position of scythe. Additionally, both of the viral reapers (SA and CE) showed scythe binding. The reduced intensity of the Western blot corresponding to viral CE reaper may indicate reduced binding to scythe (compared to the other reaper proteins tested) in this assay, as total reaper or viral reaper protein was maintained constant.

Example 5

Activation of Caspase

Caspase activation was measured using three separate preparations of *Drosophila* Reaper-GST, San Angelo virus reaper-GST (SA), and California Encephalitis virus reaper-GST(CE) (prepared and purified as described above). GST was used as a control.

Cell-free extracts were prepared from *Xenopus* oocytes as described in Thress et al., *EMBO J*, 17:6135 (1998), at page 6141. While it is known that these cell-free extracts will spontaneously release mitochondrial cytochrome c and activate endogenous caspases after prolonged incubation at room temperature, it has further been shown that the addition of *drosophila* Reaper measurably accelerates this process, triggering mitochondrial cytochrome c release, caspase activation, and fragmentation of added nuclei. (Newmeyer et al., *Cell* 79:353 (1994); Evans et al., *EMBO J.* 16:7372 (1997)).

Briefly to assess the ability of a reaper or viral reaper protein to induce caspase release, and thus by inference induce apoptosis, 10 ul of GST-reaper or GST-viral reaper protein (released from GST beads with glutathione under standard conditions) at ~0.5 to 1 mg/ml was mixed with 100 ul *Xenopus* oocyte extract. This mixture was incubated for up to 7 hr and assayed for caspase activation a specific times. To measure the caspase activity in the incubation mixtures, 3 μl of each incubation sample were mixed and incubated with 90 μl of assay buffer (50 mM HEPES pH 7.5, 100 mM NaCl, 0.1% CHAPS, 10 mM DTT, 1 mM EDTA, 10% glycerol) and the colorimetric substrate Ac-DEVD-pNA (final concentration 200 μM) [BioMol Caspase-3 assay system; BioMol Research Laboratories Inc., Plymouth Meeting, Pa.] at 37° C. At various time points, absorbance was measured at 405 nm; the measure of absorbance is directly proportional to caspase activation.

Figure 3:
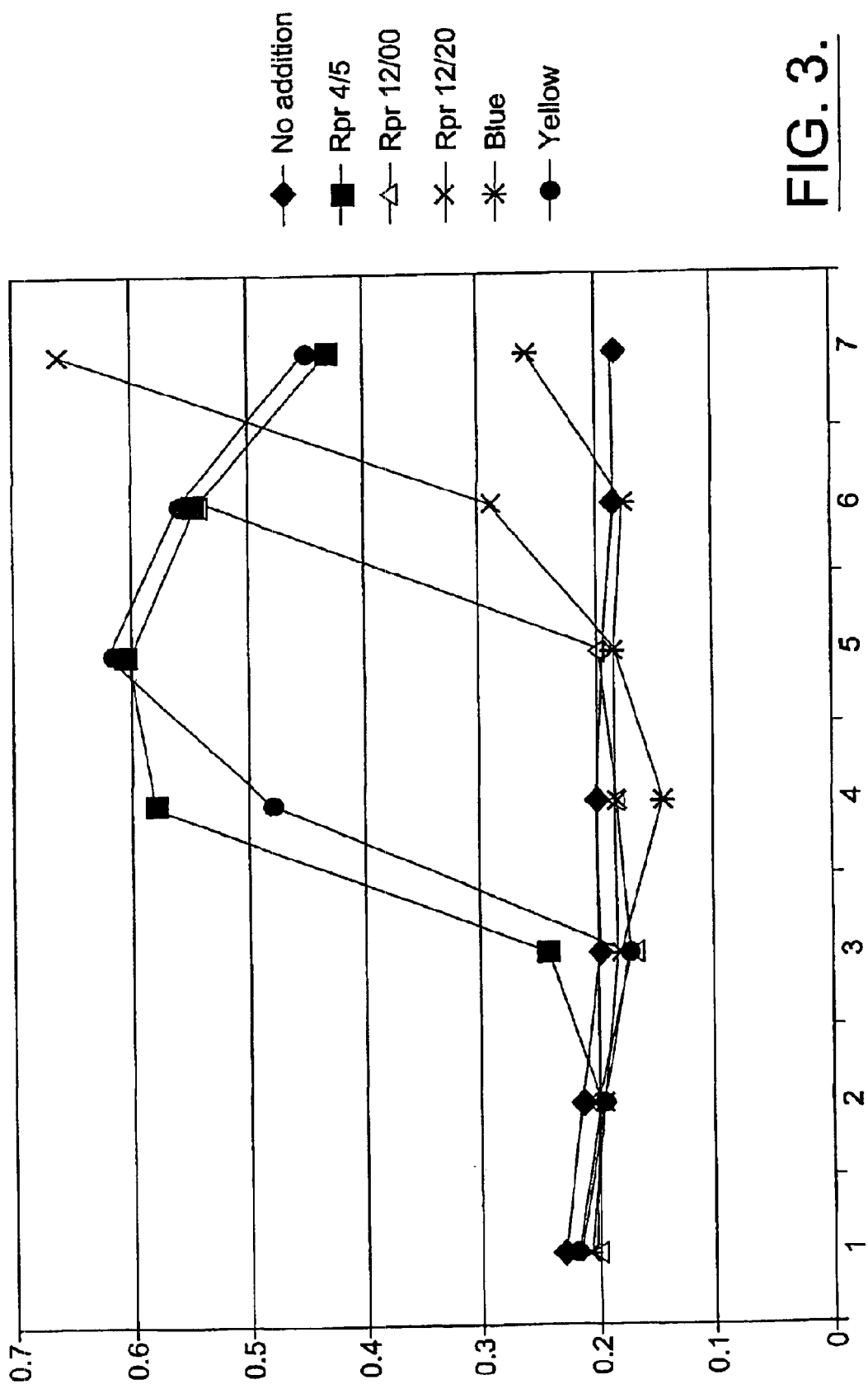
FIG. 3 graphs the results of a colorimetric assay to detect caspase activation in Xenopus cell-free extracts with added *Drosophila* reaper (Rpr 4/5, Rpr 12/00, Rpr 12/20), San Angelo virus reaper (SA), and California Encephalitis virus reaper (CE). Glutathione-S-transferase (GST) was used as a control. The Y-axis shows absorbance at 405 nm; the X-axis=time in hours.

As shown by FIG. 3 (Y-axis=absorbance at 405 nm; X-axis=time (in hours), the GST control did not result in activation of caspase, while each of the three *Drosophila* reaper preparations activated caspase, although the time at which activation was first detected varied among the reaper preparations. Both of the viral reaper preparations resulted in caspase activation. The SA virus reaper activated caspase over a time course similar to that of the Reaper ⅘ preparation in this assay. The CE virus reaper resulted in initial caspase activation at the 6–7 hour timepoint, however, the experiment did not extend beyond this time point.

That which is claimed is:

1. A method of screening a compound to determine whether the compound affects caspase activation induced by a viral reaper protein, said method comprising:
   a) obtaining a vertebrate cell extract in which the addition of isolated viral reaper protein induces detectable caspase activation;
   b) adding isolated viral reaper protein having at least 50% sequence similarity to SEQ ID NO:2 and capable of inducing caspase activation in a vertebrate cell, and a test compound, to said vertebrate cell extract;
   c) measuring caspase activation; and
   d) comparing caspase activation that occurs in the presence of the test compound to that which would be expected in the absence of the test compound;
   where a decrease in caspase activation compared to that which would be expected in the absence of the test compound indicates that said compound inhibits viral reaper-induced caspase activation, and an increase in caspase activation compared to that which would be expected in the absence of the test compound indicates that said test compound enhances viral reaper-induced caspase activation.

2. A method of screening a compound to determine whether the compound affects caspase activation induced by a viral reaper protein, said method comprising:
   a) obtaining a vertebrate cell extract in which the addition of isolated viral reaper protein induces detectable caspase activation;
   b) adding isolated viral reaper protein and a test compound to said vertebrate cell extract, where said isolated viral reaper protein comprises an amino acid sequence selected from SEQ ID NOs: 2–17;
   c) measuring caspase activation; and
   d) comparing caspase activation that occurs in the presence of the test compound to that which would be expected in the absence of the test compound;
   where a decrease in caspase activation compared to that which would be expected in the absence of the test compound indicates that said compound inhibits viral reaper-induced caspase activation, and an increase in caspase activation compared to that which would be expected in the absence of the test compound indicates that said test compound enhances viral reaper-induced caspase activation.

3. A method of screening a compound to determine whether the compound affects caspase activation induced by a viral reaper protein, said method comprising:
   a) obtaining a vertebrate cell extract in which the addition of isolated viral reaper protein induces detectable caspase activation;
   b) adding isolated viral reaper protein and a test compound to said vertebrate cell extract, where said isolated viral reaper protein is a non-structural protein (NSs) encoded by the viral small RNA from a virus of the Family Bunyaviridae;
   c) measuring caspase activation; and
   d) comparing caspase activation that occurs in the presence of the test compound to that which would be expected in the absence of the test compound;
   where a decrease in caspase activation compared to that which would be expected in the absence of the test compound indicates that said compound inhibits viral reaper-induced caspase activation, and an increase in caspase activation compared to that which would be expected in the absence of the test compound indicates that said test compound enhances viral reaper-induced caspase activation.

4. A method according to claim 1 where said vertebrate cell extract is obtained from *Xenopus oocytea*.

5. A method of screening a compound to determine whether the compound affects apoptosis induced by a viral reaper protein, said method comprising:

a) obtaining a population of cells, the cells of a type in which the addition of isolated viral reaper protein induces apoptosis;

b) administering isolated viral reaper protein having at least 75% sequence similarity to SEQ ID NO:2 and capable of inducing caspase activation in a vertebrate cell, and a test compound, to said cells;

c) measuring apoptosis that occurs in said cell population; and d) comparing apoptosis that occurs in the presence of the test compound to that which would be expected in the absence of the test compound;

where a decrease in apoptosis indicates that said compound inhibits viral reaper-induced apoptosis, and an increase in apoptosis a compared to that which would be expected in the absence of the test compound indicates that said test compound enhances viral reaper-induced apoptosis.

6. A method according to claim 5 wherein said population of cells consists of vertebrate cells.

7. A method of screening a compound to determine whether the compound affects apoptosis induced by a viral reaper protein, said method comprising:

a) obtaining a population of cells, the cells of a type in which the addition of isolated viral reaper protein induces apoptosis;

b) administering isolated viral reaper protein and a test compound to said cells where said isolated viral reaper protein comprises an amino acid sequence selected from SEQ ID Nos: 2–7;

c) measuring apoptosis that occurs in said cell population; and d) comparing apoptosis that occurs in the presence of the test compound to that which would be expected in the absence of the test compound;

where a decrease in apoptosis indicates that said compound inhibits viral reaper-induced apoptosis, and an increase in apoptosis compared to that which would be expected in the absence of the test compound indicates that said test compound enhances viral reaper-induced apoptosis.

8. A method of screening a compound to determine whether the compound affects apoptosis induced by a viral reaper protein, said method comprising:

a) obtaining a population of cells, the cells of a type in which the addition of isolated viral reaper protein induces apoptosis;

b) administering isolated viral reaper protein and a test compound to said cells where said isolated viral reaper protein is a non-structural protein (NSs) encoded by the viral small RNA from a virus of the Family Bunyaviridae;

c) measuring apoptosis that occurs in said cell population; and d) comparing apoptosis that occurs in the presence of the test compound to that which would be be expected in the absence of the test compound;

where a decrease in apoptosis indicates that said compound inhibits viral reaper-induced apoptosis, and an increase in apoptosis compared to that which would be expected in the absence of the test compound indicates that said test compound enhances viral reaper-induced apoptosis.

9. A method according to claim 5 wherein said isolated viral reaper protein is administered by transfecting cells with a nucleotide molecule encoding the viral reaper protein.

10. A method according to claim 5 where apoptosis is measured by a criterion selected from the group consisting of caspase activation, cell death, or cellular DNA degradation over time.

11. A method of screening a compound for viral reaper modulating activity, said method comprising:

(a) obtaining a population of cells modified to express an isolated viral reaper protein having at least 75% sequence similarity to SEQ ID NO:2, and capable of inducing caspase activation in a vertebrate cell;

(b) administering to a test population of said cells a test compound; and (c) comparing apoptosis occurring in said test population of cells to that which would be expected in a population of cells that did not receive said test compound;

where a reduction in apoptosis indicates that said test compound inhibits viral reaper-induced apoptosis, and an increase in apoptosis indicates said test compound enhances viral-reaper induced apoptosis.

12. A method according to claim 11 where said population of cells consists of insect cells.

13. A method according to claim 11 where said population of cells consists of vertebrate cells.

14. A method according to claim 11 where apoptosis is measured by a criterion selected from caspase activation, cell death, or cellular DNA degradation over time.

15. A method of screening a compound for viral reaper modulating activity, said method comprising:

(a) obtaining a population of cells modified to express an isolated viral reaper protein, where said isolated viral reaper protein comprises an amino acid sequence selected from SEQ ID NO.: 2–7;

(b) administering to a test population of said cells a test compound; and (c) comparing apoptosis occurring in said test population of cells to that which would be expected in a population of cells that did not receive said test compound;

where a reduction in apoptosis indicates that said test compound inhibits viral reaper-induced apoptosis, and an increase in apoptosis indicates said test compound enhances viral-reaper induced apoptosis.

16. A method of screening a compound for viral reaper modulating activity, said method comprising:

(a) obtaining a population of cells modified to express an isolated viral reaper protein, where said isolated viral reaper protein is a non-structural protein (NSs) encoded by the viral small RNA from a virus of the Family Bunyaviridae;

(b) administering to a test population of said cells a test compound; and (c) comparing apoptosis occurring in said test population of cells to that which would be expected in a population of cells that did not receive said test compound;

where a reduction in apoptosis indicates that said test compound inhibits viral reaper-induced apoptosis, and an increase in apoptosis indicates said test compound enhances viral-reaper induced apoptosis.

17. A method of inducing apoptosis in a vertebrate cell by administering an isolated viral reaper protein to said cell, in an amount sufficient to enhance apoptosis over that which would be seen in the absence of viral reaper protein, where said viral reaper protein is a protein having at least 75% sequence similarity to SEQ ID NO:2, and is capable of inducing caspase activation in a vertebrate cell.

18. A method according to claim 17 wherein said vertebrate cell is a mammalian cell.

19. A method according to claim 17 where administration of the viral reaper protein is by transfection with an isolated nucleic acid molecule encoding said viral reaper protein.

20. A method according to claim 17 where an expression vector containing an isolated nucleotide sequence encoding said viral reaper protein is administered to said cell.

21. A method of inducing apoptosis in a vertebrate cell by administering an isolated viral reaper protein to said cell, in an amount sufficient to enhance apoptosis over that which would be seen in the absence of viral reaper protein, where said isolated viral reaper protein is a non-structural protein (NSs) encoded by the viral small RNA from a virus of the Family Bunyaviridae.

* * * * *

SEQUENCE LISTING

<160> NUMBER OF SEQ ID NOS: 34

<210> SEQ ID NO 1
<211> LENGTH: 65
<212> TYPE: PRT
<213> ORGANISM: Drosophila melanogaster

<400> SEQUENCE: 1

Met Ala Val Ala Phe Tyr Ile Pro Asp Gln Ala Thr Leu Leu Arg Glu
 1               5                  10                  15

Ala Glu Gln Lys Glu Gln Gln Ile Leu Arg Leu Arg Glu Ser Gln Trp
            20                  25                  30

-continued

```
Arg Phe Leu Ala Thr Val Val Leu Glu Thr Leu Arg Gln Tyr Thr Ser
            35                  40                  45

Cys His Pro Lys Thr Gly Arg Lys Ser Gly Lys Tyr Arg Lys Pro Ser
        50                  55                  60

Gln
65

<210> SEQ ID NO 2
<211> LENGTH: 92
<212> TYPE: PRT
<213> ORGANISM: Artificial Sequence
<220> FEATURE:
<223> OTHER INFORMATION: Description of Artificial Sequence: Majority
      viral reaper sequence

<400> SEQUENCE: 2

Met Met Ser His Pro Gln Val Gln Met Asp Leu Ile Leu Met Gln Gly
  1               5                  10                  15

Met Trp His Leu Val Leu Asn Met Gly Asn Leu Ser Ile Cys Gln Pro
                 20                  25                  30

Leu Gly Ser Ser Ser Leu Met Pro Gln Lys Pro Lys Leu Leu Ser Leu
            35                  40                  45

Val Ser Arg Arg Gly Lys Leu Ile Leu Asn Leu Glu Ser Gly Arg Trp
        50                  55                  60

Arg Leu Ser Ile Ile Ile Phe Leu Glu Thr Gly Thr Thr Gln Leu Val
 65                  70                  75                  80

Thr Thr Ile Leu Pro Ser Thr Gly Phe Gln Asp Ile
                 85                  90

<210> SEQ ID NO 3
<211> LENGTH: 97
<212> TYPE: PRT
<213> ORGANISM: San Angelo virus

<400> SEQUENCE: 3

Met Met Ser His Gln Pro Val Gln Met Asp Leu Ile Leu Met Gln Gly
  1               5                  10                  15

Ile Trp His Ser Val Leu Asn Met Gly Ser Arg Ser Val Cys Leu Gln
                 20                  25                  30

Leu Gly Ser Ser Ser Met Pro Gln Lys Pro Lys Leu Leu Ser Arg
            35                  40                  45

Val Asn Gln Arg Gly Lys Gln Ile Leu Asn Leu Ala Ser Gly Arg Trp
        50                  55                  60

Arg Leu Ser Ile Ile Ile Phe Leu Glu Thr Gly Thr Ile Gln Leu Thr
 65                  70                  75                  80

Thr Ser Ile Leu Pro Ser Thr Asp Cys Leu Asp Thr Trp Leu Asp Gly
                 85                  90                  95

Phe

<210> SEQ ID NO 4
<211> LENGTH: 90
<212> TYPE: PRT
<213> ORGANISM: Snowshoe hare virus

<400> SEQUENCE: 4

Met Met Ser His Gln Gln Val Gln Met Asp Leu Ile Leu Met Gln Gly
  1               5                  10                  15

Ile Trp His Ser Val Leu Asn Met Gln Asn Gln Ser Ile Leu Leu Gln
```

```
                    20                  25                  30

Leu Gly Ser Ser Ser Met Pro Arg Pro Arg Leu Leu Ser Arg Val
        35                  40                  45

Ser Gln Arg Gly Arg Gln Ile Leu Asn Leu Glu Ser Gly Arg Trp Arg
    50                  55                  60

Leu Ser Ile Ile Ile Phe Leu Glu Thr Gly Thr Gln Leu Thr Thr
65                  70                  75                  80

Ile Leu Pro Ser Thr Asp Cys Gln Asp Ile
                85                  90
```

<210> SEQ ID NO 5
<211> LENGTH: 92
<212> TYPE: PRT
<213> ORGANISM: La Crosse virus

<400> SEQUENCE: 5

```
Met Met Ser His Gln Gln Val Gln Met Asp Leu Ile Leu Met Gln Gly
1               5                   10                  15

Ile Trp Thr Ser Val Leu Lys Met Gln Asn His Ser Thr Leu Leu Gln
                20                  25                  30

Leu Gly Ser Ser Ser Met Leu Gln Arg Pro Arg Leu Leu Ser Arg
        35                  40                  45

Val Ser Gln Arg Gly Arg Leu Thr Leu Asn Leu Glu Ser Gly Arg Trp
    50                  55                  60

Arg Leu Ser Ile Ile Ile Phe Leu Glu Thr Gly Thr Thr Gln Leu Val
65                  70                  75                  80

Thr Thr Ile Leu Pro Ser Thr Asp Tyr Leu Gly Ile
                85                  90
```

<210> SEQ ID NO 6
<211> LENGTH: 97
<212> TYPE: PRT
<213> ORGANISM: California encephalitis virus

<400> SEQUENCE: 6

```
Met Met Ser His Pro Gln Val Gln Met Asp Leu Ile Leu Met Gln Gly
1               5                   10                  15

Met Trp Thr Ser Val Leu Asn Met Gly Asn Gln Leu Thr Leu Leu Gln
                20                  25                  30

Leu Gly Ser Ser Ser Met Pro Gln Arg Pro Arg Leu Leu Ser Arg
        35                  40                  45

Val Ser Gln Arg Gly Lys Leu Ile Leu Asn Leu Ala Ser Gly Arg Trp
    50                  55                  60

Arg Leu Ser Ile Ile Ile Gly Gln Gln Thr Gly Thr Ile Gln Leu Val
65                  70                  75                  80

Thr Thr Ile Leu Pro Ser Thr Ala Ser Gln Asp Thr Leu Pro Asp Gly
                85                  90                  95

Ser
```

<210> SEQ ID NO 7
<211> LENGTH: 92
<212> TYPE: PRT
<213> ORGANISM: Jerry Slough virus

<400> SEQUENCE: 7

```
Met Met Ser His Pro Gln Val Gln Met Asp Leu Ile Gln Met Gln Gly
1               5                   10                  15
```

-continued

```
Leu Trp His Leu Trp Leu Thr Thr Glu Ser Leu Ser Ile Cys Gln Pro
            20                  25                  30

Leu Gly Ser Ser Ser Leu Met Gln Gln Lys Pro Lys Leu Leu Ser Leu
        35                  40                  45

Val Asn Arg Ser Gly Lys Leu Leu Ser Leu Glu Ser Gly Arg Trp
 50                  55                  60

Arg Ser Ser Ile Ile Ile Phe Leu Glu Thr Gly Thr Thr Gln Leu Val
 65                  70                  75                  80

Thr Thr Ile Leu Pro Ser Ile Gly Phe Gln Asp Ile
                85                  90
```

<210> SEQ ID NO 8
<211> LENGTH: 92
<212> TYPE: PRT
<213> ORGANISM: Jamestown Canyon virus

<400> SEQUENCE: 8

```
Met Met Ser His Pro Gln Val Gln Met Asp Leu Ile Gln Met Gln Gly
 1               5                  10                  15

Leu Trp His Leu Trp Leu Thr Thr Glu Ser Leu Ser Ile Cys Gln Pro
            20                  25                  30

Leu Gly Ser Ser Ser Leu Met Gln Gln Lys Pro Lys Leu Leu Ser Leu
        35                  40                  45

Val Asn Arg Ser Gly Lys Leu Leu Ser Leu Glu Ser Gly Arg Trp
 50                  55                  60

Arg Ser Ser Ile Ile Ile Phe Leu Glu Thr Gly Thr Thr Gln Leu Val
 65                  70                  75                  80

Thr Thr Ile Leu Pro Ser Ile Gly Phe Gln Asp Ile
                85                  90
```

<210> SEQ ID NO 9
<211> LENGTH: 92
<212> TYPE: PRT
<213> ORGANISM: Keystone virus

<400> SEQUENCE: 9

```
Met Met Ser His Pro Gln Val Gln Met Asp Leu Ile Leu Met Gln Gly
 1               5                  10                  15

Met Trp His Leu Trp Leu Thr Met Gly Ser Arg Ser Val Cys Gln Pro
            20                  25                  30

Leu Gly Ser Ser Ser Leu Met Pro Gln Lys Pro Lys Leu Leu Ser Leu
        35                  40                  45

Val Ser Arg Ser Gly Arg Leu His Leu Ser Leu Glu Ser Gly Arg Trp
 50                  55                  60

Arg Ser Ser Ile Ile Ile Phe Leu Glu Thr Gly Thr Thr Gln Leu Val
 65                  70                  75                  80

Thr Thr Ile Leu Pro Cys Thr Gly Phe Gln Asp Ile
                85                  90
```

<210> SEQ ID NO 10
<211> LENGTH: 97
<212> TYPE: PRT
<213> ORGANISM: Melao virus

<400> SEQUENCE: 10

```
Met Met Ser His Gln Gln Val Gln Met Asp Leu Ile Gln Met Gln Gly
 1               5                  10                  15

Ile Trp His Leu Gln Leu Arg Met Gly Lys Leu Ser Ile Cys Gln Pro
```

```
                    20                  25                  30

Leu Gly Ser Ser Ser Leu Met Pro Gln Lys Pro Lys Leu Leu Ser Leu
            35                  40                  45

Val Asn Arg Arg Gly Lys Leu Leu Asn Leu Glu Thr Gly Arg Trp
    50                  55                  60

Lys Leu Ser Thr Ile Ile Phe Leu Glu Thr Gly Thr Thr Gln Leu Val
65                  70                  75                  80

Thr Thr Ile Leu Pro Ser Ile Gly Phe Gln Asp Ile Leu Pro Asp Gly
                85                  90                  95

Cys

<210> SEQ ID NO 11
<211> LENGTH: 97
<212> TYPE: PRT
<213> ORGANISM: Trivittatus virus

<400> SEQUENCE: 11

Met Met Leu His Gln Gln Val Gln Thr Asp Leu Ile Pro Met Gln Gly
1               5                   10                  15

Met Trp His Leu Leu His Met Pro Asp Arg Thr Ile Phe Leu Leu
            20                  25                  30

Leu Gly Ser Ser Ser Met Leu Pro Arg Pro Arg Met Leu Ser Arg
            35                  40                  45

Glu Asn Gln Arg Gly Arg Leu Val Leu Asn Leu Ala Ser Gly Arg Trp
    50                  55                  60

Arg Trp Ser Ile Ile Ile Phe Leu Ala Thr Gly Thr Ile Gln Leu Val
65                  70                  75                  80

Thr Thr Ile Leu Pro Ser Thr Glu Phe Gln Ala Ile Ser Gln Asp Gly
                85                  90                  95

Phe

<210> SEQ ID NO 12
<211> LENGTH: 97
<212> TYPE: PRT
<213> ORGANISM: Morro Bay virus

<400> SEQUENCE: 12

Met Met Ser His Pro Gln Val Gln Met Asp Leu Ile Leu Met Gln Gly
1               5                   10                  15

Met Trp Thr Ser Val Leu Asn Met Gly Asn Arg Leu Thr Leu Leu Gln
            20                  25                  30

Leu Gly Ser Ser Ser Met Pro Gln Lys Pro Arg Leu Leu Ser Arg
            35                  40                  45

Val Ser Gln Arg Gly Lys Leu Ile Leu Asn Leu Ala Ser Gly Arg Trp
    50                  55                  60

Arg Leu Ser Ile Ile Ile Phe Gln Gln Thr Gly Thr Ile Gln Leu Val
65                  70                  75                  80

Thr Thr Ile Leu Pro Ser Thr Ala Ser Gln Asp Thr Leu Pro Asp Gly
                85                  90                  95

Ser

<210> SEQ ID NO 13
<211> LENGTH: 92
<212> TYPE: PRT
<213> ORGANISM: Inkoo virus

<400> SEQUENCE: 13
```

```
Met Met Ser His Pro Gln Val Gln Met Asp Leu Ile Gln Met Gln Gly
  1               5                  10                  15

Leu Trp His Leu Trp Leu Thr Met Glu Asn Leu Leu Ile Trp Gln Pro
             20                  25                  30

Leu Gly Ser Ser Leu Met Gln Gln Lys Pro Lys Leu Leu Ser Leu
         35                  40                  45

Val Asn Arg Ser Gly Lys Leu Leu Asn Leu Glu Ser Gly Arg Trp
 50                      55                  60

Arg Leu Ser Ile Ile Ile Phe Leu Glu Thr Gly Thr Thr Gln Leu Val
 65                  70                  75                  80

Thr Thr Ile Leu Pro Ser Thr Gly Phe Leu Asp Thr
                 85                  90

<210> SEQ ID NO 14
<211> LENGTH: 92
<212> TYPE: PRT
<213> ORGANISM: Serra do Navio virus

<400> SEQUENCE: 14

Met Met Ser His Gln Pro Val Gln Met Asp Leu Ile Gln Met Gln Gly
  1               5                  10                  15

Leu Trp His Leu Trp Leu Val Met Gly Ser Arg Ser Ile Leu Gln Pro
             20                  25                  30

Leu Glu Ser Ser Ser Leu Met Pro Gln Lys Pro Lys Leu Leu Ser Leu
             35                  40                  45

Ala Ser Arg Arg Gly Lys Leu Leu Ser Leu Glu Thr Gly Arg Trp
 50                      55                  60

Arg Leu Ser Ile Ile Ile Phe Leu Glu Thr Gly Thr Thr Gln Leu Val
 65                  70                  75                  80

Thr Thr Ile Leu Pro Ser Thr Glu Phe Gln Asp Ile
                 85                  90

<210> SEQ ID NO 15
<211> LENGTH: 92
<212> TYPE: PRT
<213> ORGANISM: South River virus

<400> SEQUENCE: 15

Met Met Ser His Pro Gln Val Gln Met Asp Leu Ile Gln Met Gln Gly
  1               5                  10                  15

Leu Trp His Leu Trp Leu Thr Met Glu Asn Leu Ser Ile Cys Gln Pro
             20                  25                  30

Leu Gly Ser Ser Leu Met Gln Gln Lys Pro Lys Leu Leu Ser Leu
         35                  40                  45

Val Asn Arg Ser Gly Arg Leu Ile Leu Asn Leu Glu Ser Gly Arg Trp
 50                      55                  60

Arg Leu Ser Ile Ile Ile Phe Leu Glu Thr Gly Thr Thr Gln Leu Val
 65                  70                  75                  80

Thr Thr Ile Leu Pro Ser Thr Gly Phe Leu Asp Ile
                 85                  90

<210> SEQ ID NO 16
<211> LENGTH: 97
<212> TYPE: PRT
<213> ORGANISM: Lumbo virus

<400> SEQUENCE: 16
```

-continued

```
Met Met Ser His Pro Pro Val Gln Met Asp Leu Ile Leu Met Gln Gly
  1               5                  10                  15

Met Trp Thr Phe Val Leu Asn Met Glu Asn Gln Ser Ile Ser Ile Pro
             20                  25                  30

Leu Gly Ser Phe Ser Leu Met Pro Leu Arg Pro Arg Leu Leu Ser Leu
         35                  40                  45

Val Ser Arg Arg Gly Arg Leu Val Leu Asn Leu Glu Ser Gly Arg Trp
 50                  55                  60

Arg Ser Ser Ile Ile Ile Phe Leu Glu Thr Gly Thr Thr Gln Leu Ile
 65                  70                  75                  80

Thr Thr Ile Leu Pro Ser Thr Gly Cys Gln Gly Ile Trp Leu Asp Gly
             85                  90                  95

Cys
```

<210> SEQ ID NO 17
<211> LENGTH: 97
<212> TYPE: PRT
<213> ORGANISM: Tahyna virus

<400> SEQUENCE: 17

```
Met Met Ser His Pro Pro Val Gln Met Asp Leu Ile Leu Met Gln Gly
  1               5                  10                  15

Met Trp Thr Ser Val Leu Asn Met Gly Lys Gln Leu Ile Ser Ile Pro
             20                  25                  30

Leu Gly Ser Ser Ser Leu Met Pro Gln Lys Pro Lys Leu Leu Ser Leu
         35                  40                  45

Val Ser Arg Arg Gly Arg Leu Val Leu Asn Leu Glu Ser Gly Arg Trp
 50                  55                  60

Arg Ser Ser Ile Ile Ile Phe Leu Glu Thr Gly Thr Thr Gln Leu Ile
 65                  70                  75                  80

Thr Thr Ile Leu Pro Ser Thr Gly Cys Thr Gly Ile Trp Leu Asp Gly
             85                  90                  95

Cys
```

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: portion of
      Drosophila melanogaster Grim protein

<400> SEQUENCE: 18

```
Met Ala Ile Ala Phe Tyr Ile Pro Asp Gln Ala Gln Leu Leu Ala Arg
  1               5                  10                  15

Ser Tyr Gln Gln Asn Gly Gln
             20
```

<210> SEQ ID NO 19
<211> LENGTH: 198
<212> TYPE: DNA
<213> ORGANISM: Drosophila melanogaster

<400> SEQUENCE: 19

```
atggcagtgg cattctacat acccgatcag gcgactctgt tgcgggaggc ggagcagaag    60
gagcagcaga ttctccgctt gcgggagtca cagtggagat cctggccac cgtcgtcctg   120 gaaaccctgc gccagtacac ttcatgtcat ccgaagaccg gaagaaagtc cggcaaatat   180
```
gcgaagccat cgcaatga                                              198

<210> SEQ ID NO 20
<211> LENGTH: 294
<212> TYPE: DNA
<213> ORGANISM: San Angelo virus

<400> SEQUENCE: 20
atgatgtcgc atcaaccggt gcaaatggat ttgatcctga tgcagggtat ctggcattct    60
gtgttaaaca tggggagtcg atcagtttgt cttcagttag gatcttcttc ctcaatgccg   120
caaaagccaa agctgctctc tcgcgtaaac cagagaggaa agcaaatcct aaatttggcg   180
agtggcaggt ggagattgtc aataatcatt ttcctggaaa caggaacaat ccaattgaca   240
acctcgatct taccatccac agattgtctg gatacctggc tagatgggtt ctag         294

<210> SEQ ID NO 21
<211> LENGTH: 279
<212> TYPE: DNA
<213> ORGANISM: Snowshoe hare virus

<400> SEQUENCE: 21
atgatgtcgc atcaacaggt gcaaatggat ttgatcctga tgcagggtat atggcattct    60
gtgttaaata tgcagaatca gtcaatcttg ctgcagttag gatcttcttc ctcaatgccg   120
caaaggccaa ggctgctctc tcgcgtaagc cagagaggaa ggcaaatcct aaatttggag   180
agtggcaggt ggaggttgtc aataatcatt ttcctggaaa caggaacaat ccaattaaca   240
gcgacgatct taccatccac agattgtcag gatatttag                         279

<210> SEQ ID NO 22
<211> LENGTH: 279
<212> TYPE: DNA
<213> ORGANISM: LaCrosse Virus

<400> SEQUENCE: 22
atgatgtcgc atcaacaggt gcaaatggat ttgatcctga tgcagggtat atggacttct    60
gtgttaaaaa tgcagaatca ctcaaccttg ctgcagttag gatcttcttc ctcaatgctg   120
caaaggccaa ggctgctctc tcgcgtaagc cagagaggaa ggctaaccct aaatttggag   180
agtggcaggt ggaggttatc aataatcatt ttcctggaaa caggaacaac ccaattggta   240
acaacgatct taccatccac agattatctg ggtatttag                         279

<210> SEQ ID NO 23
<211> LENGTH: 294
<212> TYPE: DNA
<213> ORGANISM: California encephalitis virus

<400> SEQUENCE: 23
atgatgtcgc atccacaggt gcaaatggat ttgatcctga tgcagggtat gtggacttct    60
gtgctaaaca tggggaatca attaaccttg ctgcagttag gatcttcttc ctcaatgccg   120
caaaggccaa ggctgctctc tcgcgtaagc cagagaggaa agctaatcct aaatttggcg   180
agtggcaggt ggaggttgtc aataatcatt ttccagcaaa caggaacaat ccaattggta   240
acaacgatct taccatccac cgcatctcag gataccttgc cagatgggtc ctag         294

<210> SEQ ID NO 24
<211> LENGTH: 279
<212> TYPE: DNA
<213> ORGANISM: Jerry Slough virus

<400> SEQUENCE: 24

```
atgatgtcgc atccacaggt gcaaatggat ttgatccaga tgcagggttt gtggcattta    60
tggctgacca cggagagtct atcaatctgt cagccgttag gatcttcttc cttaatgcag   120
caaaagccaa agctgctctc gctcgtaaac cggagcggaa agctactcct aagtttggag   180
agtggcaggt ggagatcatc aataatcatt ttcctggaaa caggaacaac ccaattggta   240
acaacgatct taccatccat aggctttcag gatatctag                          279
```

<210> SEQ ID NO 25
<211> LENGTH: 279
<212> TYPE: DNA
<213> ORGANISM: Jamestown Canyon virus

<400> SEQUENCE: 25

```
atgatgtcgc atccacaggt gcaaatggat ttgatccaga tgcagggttt gtggcattta    60
tggctgacca cggagagtct atcaatctgt cagccgttag gatcttcttc cttaatgcag   120
caaaagccaa agctgctctc gctcgtaaac cggagcggaa agctactcct aagtttggag   180
agtggcaggt ggagatcgtc aataatcatt tttctggaaa caggaacaac ccaattggta   240
acaacgatct taccatccat aggctttcag gatatctag                          279
```

<210> SEQ ID NO 26
<211> LENGTH: 279
<212> TYPE: DNA
<213> ORGANISM: Keystone virus

<400> SEQUENCE: 26

```
atgatgtcgc atccacaggt gcaaatggat ttgatcctga tgcagggtat gtggcattta    60
tggctaacca tggggagtcg atcagtctgt caaccgttag gatcttcttc cttaatgccg   120
caaaagccaa agctgctctc actcgtaagc cggagcggaa ggctacacct aagtttggag   180
agtggcaggt ggagatcgtc aataatcatt ttcctggaaa caggaacaac ccaattggta   240
acaacgatct taccttgcac cggatttcag gatatctag                          279
```

<210> SEQ ID NO 27
<211> LENGTH: 294
<212> TYPE: DNA
<213> ORGANISM: Melao virus

<400> SEQUENCE: 27

```
atgatgtcgc atcaacaggt gcaaatggat ttgatccaga tgcagggtat ctggcattta    60
caattgcgca tggggaagct atcaatttgt cagccgttag gatcttcttc cttaatgccg   120
caaaagccaa agctgctctc tctcgtaaac cggagaggaa agctactcct aaatttggag   180
actggcaggt ggaaattgtc aacaatcatt ttcctggaaa caggaacaac ccaattggta   240
acaacgatct taccatccat cggctttcag gatatcttgc cagatgggtg ctag         294
```

<210> SEQ ID NO 28
<211> LENGTH: 294
<212> TYPE: DNA
<213> ORGANISM: Trivittatus virus

<400> SEQUENCE: 28

```
atgatgctcc atcaacaggt gcaaacggat ttgatcccga tgcagggtat gtggcattta    60
ttgctgcaca tgccggatcg tacgatcttt ctgctgttag gatcttcttc ctcaatgctg   120
```

```
ccaaggccaa gaatgctctc tcgagaaaac cagaggggaa ggttagtatt aaatttggcg      180
agtggtcggt ggaggtggtc aataatcatt ttcctggcaa caggaacaat ccaattggta      240
acaacgatct taccatccac agaatttcag gctatctcgc aagatgggtt ctag            294
```

<210> SEQ ID NO 29
<211> LENGTH: 294
<212> TYPE: DNA
<213> ORGANISM: Morro Bay virus

<400> SEQUENCE: 29

```
atgatgtcgc atccacaggt gcaaatggat ttgatcctga tgcagggtat gtggacttct       60
gtgctaaaca tggggaatcg attaaccttg ctgcagttag gatcttcttc ctcaatgccg      120
caaaagccaa ggctgctctc tcgcgtaagc cagagaggaa agctaatcct aaatttggcg      180
agtggcaggt ggagattgtc aataatcatt ttccagcaaa caggaacaat ccaattggta      240
acaacgatct taccatccac cgcatctcag gataccttgc cagatgggtc ctag            294
```

<210> SEQ ID NO 30
<211> LENGTH: 279
<212> TYPE: DNA
<213> ORGANISM: Inkoo virus

<400> SEQUENCE: 30

```
atgatgtcgc atccacaggt gcaaatggat ttgatccaga tgcagggttt gtggcattta       60
tggctgacca tggagaatct attaatttgg cagccgttag gatcttcttc cttaatgcag      120
caaaagccaa agctgctctc gctcgtaaac cggagcggaa agctactcct aaatttggag      180
agtggcaggt ggagattgtc aataatcatt ttcctggaaa caggaacaac ccaattggta      240
acaacgatct taccatccac cggctttctg gatacttag                             279
```

<210> SEQ ID NO 31
<211> LENGTH: 279
<212> TYPE: DNA
<213> ORGANISM: Serra do Navio virus

<400> SEQUENCE: 31

```
atgatgtcgc atcaaccggt gcaaatggat ttgatccaga tgcagggttt gtggcattta       60
tggctggtca tggggagtcg atcaatctta cagccgttag aatcttcttc cttaatgccg      120
caaaagccaa agctgctctc tctcgcaagc cggagaggaa agctactcct aagtttggag      180
actggcaggt ggagattgtc aataatcatt ttcctggaaa caggaacaac ccaattggta      240
acaacgatct taccatccac agaatttcag gatatttag                             279
```

<210> SEQ ID NO 32
<211> LENGTH: 279
<212> TYPE: DNA
<213> ORGANISM: South River virus

<400> SEQUENCE: 32

```
atgatgtcgc atccacaggt gcaaatggat ttgatccaga tgcagggttt gtggcattta       60
tggctgacca tggagaatct atcaatctgt cagccgttag gatcttcttc cttaatgcag      120
caaaagccaa agctgctctc gctcgtaaac cggagcggaa ggctaatcct aaatttggag      180
agtggcaggt ggagattgtc aataatcatt ttcctggaaa caggaacaac ccaattggta      240
acaacgatct taccatccac cggctttctg gatatttag                             279
```

-continued

```
<210> SEQ ID NO 33
<211> LENGTH: 294
<212> TYPE: DNA
<213> ORGANISM: Lumbo virus

<400> SEQUENCE: 33
atgatgtcgc atccaccggt gcaaatggat ttgatcctga tgcagggtat gtggacttttt    60 gtgttaaaca tggagaatca atcaatctcc attccgttag gatcttttttc cttaatgccg   120 ctaaggccaa ggctgctctc gctcgtaagc cggagaggaa ggctagtcct aaatttggag   180
agtggcaggt ggagatcgtc aataatcatt ttcctggaaa caggaacaac ccaattgata   240
acaacgatct taccatccac cggctgtcag ggtatctggc tagatgggtg ttag          294

<210> SEQ ID NO 34
<211> LENGTH: 294
<212> TYPE: DNA
<213> ORGANISM: Tahyna virus

<400> SEQUENCE: 34
atgatgtcgc atccaccggt gcaaatggat ttgatcctga tgcagggtat gtggacttct    60
gtattaaaca tggggaagca attaatctcc attccgttag gatcttcttc cttaatgccg   120
caaaagccaa agctgctctc gctcgtaagc cggagaggaa ggctagtcct aaatttggag   180
agtggcaggt ggaggtcgtc aattatcatt ttcctggaaa caggaacaac ccaattgata   240
acaacgatct taccatccac cggctgtacg ggtatttggc tagatgggtg ctag          294
```